(12) United States Patent
Ewers et al.

(10) Patent No.: US 10,980,958 B2
(45) Date of Patent: Apr. 20, 2021

(54) SOUND MITIGATION STRUCTURES AND METHODS FOR USE IN TREATING OBSTRUCTIVE SLEEP APNEA

(71) Applicant: Fresca Medical Inc., San Clemente, CA (US)

(72) Inventors: Richard Ewers, Fulterton, CA (US); Douglas Gaylord, Carlsbad, CA (US); Carl Tedesco, Carlsbad, CA (US); Steve Harrington, Cardiff, CA (US)

(73) Assignee: FRESCA MEDICAL, Inc., San Clemente, CA (US)

( * ) Notice: Subject to any disclaimer, the term of this patent is extended or adjusted under 35 U.S.C. 154(b) by 251 days.

(21) Appl. No.: 15/910,937

(22) Filed: Mar. 2, 2018

(65) Prior Publication Data

US 2018/0185597 A1    Jul. 5, 2018

Related U.S. Application Data

(63) Continuation-in-part of application No. 15/334,243, filed on Oct. 25, 2016, now Pat. No. 10,206,571.
(Continued)

(51) Int. Cl.
*A61M 16/06* (2006.01)
*A61M 16/20* (2006.01)
(Continued)

(52) U.S. Cl.
CPC ........... *A61M 16/06* (2013.01); *A61B 5/4818* (2013.01); *A61M 16/0066* (2013.01);
(Continued)

(58) Field of Classification Search
CPC .. A61M 16/00; A61M 16/06; A61M 16/0066; A61M 16/0069; A61M 16/024;
(Continued)

(56) References Cited

U.S. PATENT DOCUMENTS

2003/0214082 A1* 11/2003 Jones ................. F01M 13/0416
  264/523
2009/0241965 A1* 10/2009 Sather ................... A61M 15/08
  128/207.18
(Continued)

OTHER PUBLICATIONS

International Search Report and Written Opinion dated May 8, 2018 in PCT/US2018/020772 (8 pages).

*Primary Examiner* — Valerie L Woodward
*Assistant Examiner* — Paige Kathleen Bugg
(74) *Attorney, Agent, or Firm* — Manuel F. de la Cerra

(57) ABSTRACT

A sleep mask valve structure for treating a patient suffering from obstructive sleep apnea is provided. The valve structure includes a rigid valve housing comprising an inspiratory valve and an adjustable expiratory valve. The housing defines an outside mask side and an intra-mask side, and further defines an expiratory airflow conduit accommodating airflow from the intra-mask side to the outside mask side and an inspiratory airflow conduit accommodating airflow from the outside mask side to the intra-mask side. The expiratory airflow conduit includes at least two changes of direction, with each direction change greater than or equal to 75 degrees, and the inspiratory airflow conduit includes at least one change of direction greater than or equal to 75 degrees. The two paths share at least one change of direction.

16 Claims, 16 Drawing Sheets

Related U.S. Application Data

(60) Provisional application No. 62/465,905, filed on Mar. 2, 2017, provisional application No. 62/311,804, filed on Mar. 22, 2016.

(51) Int. Cl.
 *A61B 5/00* (2006.01)
 *A61M 16/00* (2006.01)

(52) U.S. Cl.
 CPC ........ *A61M 16/201* (2014.02); *A61M 16/0003* (2014.02); *A61M 2205/42* (2013.01); *A61M 2206/14* (2013.01); *A61M 2230/205* (2013.01)

(58) Field of Classification Search
 CPC ............ A61M 16/201; A61M 16/0816; A61M 16/0875; A61M 16/0003; A61M 16/20; A61M 2016/0027; A61M 2205/42; A61M 2206/14; A61M 2230/205; A61B 5/00; A61B 5/4818
 See application file for complete search history.

(56) References Cited

U.S. PATENT DOCUMENTS

| | | | |
|---|---|---|---|
| 2012/0138058 A1* | 6/2012 | Fu | A61M 16/0066 128/204.23 |
| 2012/0325205 A1* | 12/2012 | Allum | A61M 16/0622 128/201.13 |
| 2012/0325218 A1* | 12/2012 | Brambilla | A61M 16/0875 128/205.25 |
| 2013/0160769 A1 | 6/2013 | Ng et al. | |
| 2014/0116429 A1 | 5/2014 | Patil et al. | |
| 2016/0001104 A1* | 1/2016 | Lewin | F16K 31/12 128/205.24 |
| 2016/0084394 A1* | 3/2016 | Wyatt | F16K 17/0433 220/203.27 |
| 2016/0095996 A1* | 4/2016 | Gusky | A61M 16/08 128/205.25 |
| 2016/0158477 A1* | 6/2016 | Dhuper | A61M 16/204 128/200.23 |
| 2016/0317780 A1* | 11/2016 | Cole | A61M 16/0875 |
| 2018/0015243 A1* | 1/2018 | Lee | A61M 16/06 |

\* cited by examiner

Fresh Air

Blower Air

INSPIRATION MODE

Patient Exhalation

Blower Air

EXPIRATION MODE

Blower Air

Blower Air

APNEA MODE

SOUND MITIGATION STRUCTURES AND METHODS FOR USE IN TREATING OBSTRUCTIVE SLEEP APNEA

RELATED APPLICATIONS

This application claims priority to U.S. Provisional Application No. 62/465,905, filed Mar. 2, 2017, titled "Sound Mitigation/Flow Optimization in a Valved Obstructive Sleep Apnea Treatment Mask", the entire contents of which is incorporated herein in its entirety.

The assignee of this application, FRESCA Medical, has described various embodiments of its valved Positive Airway Pressure (PAP) sleep apnea treatment mask. Those embodiments are described in U.S. patent application Ser. No. 13/860,926, filed Apr. 11, 2013, titled "Sleep Apnea Device," U.S. Provisional Application Ser. No. 61/623,855, filed Apr. 13, 2012, titled "Sleep Apnea Device," U.S. Provisional Application Ser. No. 61/775,430, filed Mar. 8, 2013, titled "Sleep Apnea Device," U.S. Provisional Application No. 61/823,553, filed May 15, 2013, titled "Sleep Apnea Device," U.S. Provisional Application No. 61/838,191, filed Jun. 21, 2013, titled "Sleep Apnea Device," U.S. Provisional Application No. 61/962,501, filed Nov. 8, 2013, titled "Sleep Apnea Device," U.S. Provisional Application No. 61/909,956, filed Nov. 27, 2013, titled "Sleep Apnea Device," U.S. Provisional Application No. 61/927,355, filed Jan. 14, 2014, titled "Valve with Pressure Feedback," U.S. Provisional Application No. 62/134,506, filed Mar. 17, 2015, titled "Valve with Pressure Feedback Draft Provisional Application," U.S. Provisional Application No. 62/163,601, filed May 19, 2015, titled "Airflow Generator with Delayed Onset", U.S. Provisional Application No. 62/184,787, filed Jun. 25, 2015, titled "Sleep Apnea Device," U.S. Provisional Application No. 62/239,146, filed Oct. 8, 2015, titled "Sleep Apnea Device," U.S. patent application Ser. No. 14/930,284, filed Nov. 2, 2015, titled "Apparatus, System and Methods for Treating Obstructive Sleep Apnea", U.S. Provisional Application No. 62/246,339, filed Oct. 26, 2015, titled "Venting of a Valved CPAP Mask to Create a Comfortable Breathing Sensation", U.S. Provisional Application No. 62/246,489, filed Oct. 26, 2015, titled "Managing Sleep Apnea with Pulse Oximeters and With Additional Assessment Tools", U.S. Provisional Application No. 62/246,328, filed Oct. 26, 2015, titled "Novel Low Flow Technology Designed to Meet CPAP Efficacy", U.S. Provisional Application No. 62/246,477, filed Oct. 26, 2015, titled "Composite Construction Air Delivery Hose for USE with CPAP Treatment", U.S. Provisional Application No. 62/275,899, filed Jan. 7, 2016, titled "Valved Mask To Reduce and Prevent Snoring", U.S. Provisional Application No. 62/311,804, filed Mar. 22, 2016, titled "Improvements to Sleep Apnea Machine", U.S. Provisional Application No. 62/382,980, filed Sep. 2, 2016, titled "Dual Rotatable Hose For Use With CPAP Treatment", U.S. application Ser. No. 15/334,243, filed Oct. 15, 2016, titled "Apparatus, Systems, And Methods For Treating Obstructive Sleep Apnea", U.S. Provisional Application No. 62/532,240, filed Jul. 13, 2017, titled "Sleep Apnea Treatment System and Improvements Thereto", and U.S. Provisional Application No. 62/595,529, filed Dec. 6, 2017, titled "Sleep Apnea Treatment System and Improvements Thereto", all of which are hereby incorporated by reference in their entirety.

TECHNICAL FIELD

The present invention is related to medical systems, devices, and methods. More specifically, the invention is related to systems, devices and methods for treating obstructive sleep apnea or snoring.

BACKGROUND

Obstructive sleep apnea (OSA) is a common medical disorder that can be quite serious. It has been reported that approximately one in twenty-two Americans (about 12,000,000 people) suffer from OSA, and many cases go undiagnosed. Chronic fatigue has long been recognized as the hallmark of OSA, but more recently, large clinical studies have shown a strong link between OSA, strokes and death.

Obstructive sleep apnea is a condition in which the flow of air pauses or decreases during breathing while one is asleep, because the airway has become narrowed, blocked, or floppy. (See FIG. 1A of published patent application US20140246025 A1 to Cragg et al., published Sep. 4, 2014, which is incorporated herein by reference, illustrating an airway A during normal breathing, and FIG. 1B therein, illustrating the airway A during OSA.) A pause in breathing is called an apnea episode, while a decrease in airflow during breathing is called a hypopnea episode. Almost everyone has brief apnea or hypopnea episodes while they sleep. In OSA, however, apnea episodes occur more frequently and last longer than in the general population. OSA has become an increasingly costly medical condition in recent years, as the disorder is more prevalent in obese people, and obesity has become significantly more prevalent. Unfortunately, the currently available options for treating OSA are not ideal.

A person with OSA usually begins snoring heavily soon after falling asleep. Often, the snoring gets louder. The snoring is then interrupted by a long silent period during which there is no breathing. This is followed by a loud snort and gasp, as the person attempts to breathe. This pattern repeats. Many people wake up unrefreshed in the morning and feel sleepy or drowsy throughout the day. This is called excessive daytime sleepiness (EDS). People with sleep apnea may act grumpy or irritable, be forgetful, fall asleep while working, reading, or watching TV, feel sleepy or even fall asleep while driving, or have hard-to-treat headaches. OSA sufferers may also experience depression that becomes worse, hyperactive behavior (especially in children), or leg swelling (if severe).

The most widely used therapy for OSA is Continuous Positive Airway Pressure (CPAP). As shown in FIG. 2 of US20140246025 A1 to Cragg et al., a CPAP system typically 10 consists of a mask 12a-12c fitting in or over the nose or nose and mouth, an air pressurizing console 14 and a tube 16 connecting the two (typically a six-foot long hose with a 20 mm diameter bore). CPAP works by pressurizing the upper airway throughout the breathing cycle, essentially inflating the airway to keep it open and thus creating what is sometimes referred to as a "pneumatic splint." This flow is at set pressure that has been predetermined through medical testing to be appropriate to create a pneumatic splint in the user's airway. This prevents airway collapse and allows the user to breathe without obstruction. Because the masks 12a-12c typically leak air, CPAP systems have to provide an airflow rate of up to 200 liters per minute (approximate figure based on unpublished data). The high airflow rate is needed for multiple reasons. First, all the air needed for breathing must come through the hose. Second, conventional masks have an intended leak built in for the purpose of constant "$CO_2$ washout." Third, these systems achieve the required pressure by using a high airflow rate to generate a back-pressure at the mask end, where the air is leaking out. Unfortunately, this high flow rate makes breathing feel quite uncomfortable for many users and requires a relatively large, noisy pressurizing console 14. Additionally, the high required flow rates of CPAP often cause discomfort during exhalation due to increased resistance, as well as nasal dryness, dry mouth, ear pain, rhinitis, abdominal bloating and headaches.

The overwhelming shortcoming of CPAP is poor user compliance. Over half of all users who try CPAP stop using it. Users dislike the side effects mentioned above, as well as having to wear an uncomfortable, claustrophobic mask, being tethered to a pressurizing console, the noise of the console, traveling with a bulky device, and a loss of personal space in bed. The noise is even more problematic because it can cause discomfort to the patients sleep partner, further undermining use compliance.

It would be advantageous to mitigate the sound emanating from the mask in an effort to improve user compliance and comfort.

SUMMARY

Provided in various example embodiments is an improved apparatus, system, and method for treating obstructive sleep apnea. Specifically, a novel sleep mask valve structure for treating a patient suffering from obstructive sleep apnea is disclosed. The valve structure includes a rigid valve housing comprising an inspiratory valve and an adjustable expiratory valve. The housing defines an outside mask side and an intra-mask side, and further defines an expiratory airflow conduit accommodating airflow from the intra-mask side to the outside mask side and an inspiratory airflow conduit accommodating airflow from the outside mask side to the intra-mask side. The expiratory airflow conduit includes at least two changes of direction, with each direction change greater than or equal to 75 degrees, and the inspiratory airflow conduit includes at least one change of direction greater than or equal to 75 degrees. The two paths share at least one change of direction.

The valve structure is a removable cartridge that is adapted to be inserted into a nasal pillow or mask. It may further have a sound absorbing liner, preferably made of a material with a durometer of 5 A to 90 A. The inspiratory valve and expiratory valves may also be formed of a sound absorbing material. The outside mask side of the expiratory airflow conduit may have an edge with an irregular shape to help mitigate sound.

To further aggravate the tortuous airflow path, the expiratory airflow conduct may include a plurality of vanes that introduce an additional change of direction to the expiratory airflow conduit that is greater than or equal to 75 degrees. Those vanes may also be used within the inspiratory airflow conduit. The vanes may be curved.

The valve structure may also have an outer mask baffling screen and/or an intra-mask baffling screen. Either screen may have an outer surface with a plurality of openings that allows for airflow across the baffling screen. Preferably the plurality of openings has at least two differently sized openings, and the differently sized openings are interspersed along the outer surface. Their shapes may be, but are not limited to, circular, elongate or both.

The valve structure may also have a cover connected to the outside mask side. The cover may introduce an additional change of direction to the expiratory airflow conduit that is greater than or equal to 75 degrees. The cover may have a sound absorbing liner.

Additional aspects, alternatives and variations as would be apparent to persons of skill in the art are also disclosed herein and are specifically contemplated as included as part of the invention. The invention is set forth only in the claims as allowed by the patent office in this or related applications, and the following summary descriptions of certain examples are not in any way to limit, define or otherwise establish the scope of legal protection.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure. It will be understood that certain components and details may not appear in the figures to assist in more clearly describing the invention.

FIG. 4AA is an opposite side view of the first embodiment of the outer mask baffling screen.

FIG. 4BB is an opposite side view of the second embodiment of the outer mask baffling screen.

FIG. 4CC is an opposite side view of the third embodiment of the outer mask baffling screen.

FIG. 4DD is an opposite side view of the fourth embodiment of the outer mask baffling screen.

FIG. 4EE is an opposite side view of the fifth embodiment of the outer mask baffling screen.

FIG. 4FF is an opposite side view of the sixth embodiment of the outer mask baffling screen.

FIG. 4GG is an opposite side view of the seventh embodiment of the outer mask baffling screen.

DETAILED DESCRIPTION OF EXAMPLE EMBODIMENTS

Figure 1A:
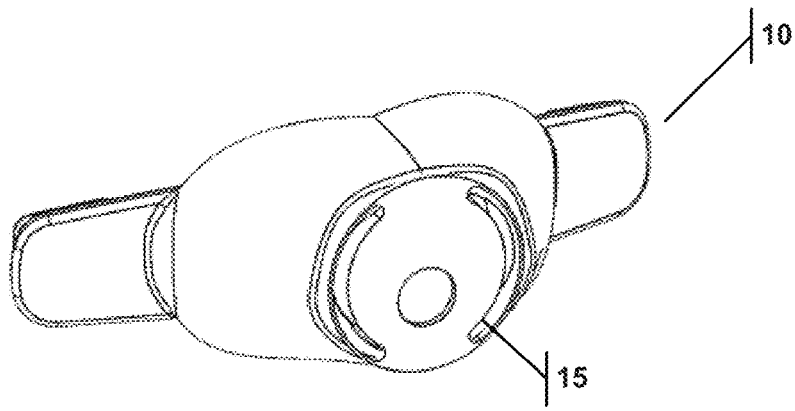
FIG. 1A illustrates a novel sleep mask and valve structure for use in the treatment of sleep apnea.

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, process operations well known to persons of skill in the art have not been described in detail in order not to obscure unnecessarily the present invention. Various techniques and mechanisms of the present invention will sometimes be described in singular form for clarity. However, it should be noted that some embodiments include multiple iterations of a technique or multiple mechanisms unless noted otherwise. Similarly, various steps of the methods shown and described herein are not necessarily performed in the order indicated, or performed at all in certain embodiments. Accordingly, some implementations of the methods discussed herein may include more or fewer steps than those shown or described. Further, the techniques and mechanisms of the present invention will sometimes describe a connection, relationship or communication between two or more entities. It should be noted that a connection or relationship between entities does not necessarily mean a direct, unimpeded connection, as a variety of other entities or processes may reside or occur between any two entities. Consequently, an indicated connection does not necessarily mean a direct, unimpeded connection, unless otherwise noted.

The following list of example features corresponds with FIGS. 1A-13B and is provided for ease of reference, where like reference numerals designate corresponding features throughout the specification and figures:

| Feature | Number |
|---|---|
| Sleep Mask | 10 |
| Sleep Mask Valve Structure | 15 |
| Sleep Mask Valve Structure Improved Design | 15A |
| Valve Housing | 20 |
| Air Conduit Outlet | 21 |
| Inspiratory Valve Seat | 22 |
| Sound Absorbing Liner | 23 |
| Expiratory Valve Seat | 24 |
| Expiratory Valve Membrane | 25 |
| Expiratory Valve Retaining Seat | 30 |
| Inspiratory Valve Retailing Seat | 35 |
| Inspiratory Membrane | 40 |
| Intra-mask Side | 42 |
| Outside-mask Side | 43 |
| Expiratory Airflow Change of Direction | 46 |
| Retaining Clip | 45 |
| Inspiratory Airflow Change of direction | 47 |
| Shared inspiratory/expiratory Change of Direction | 48 |
| Cartridge | 49 |
| Outer Mask Baffling Screen | 50 |
| Outer Surface | 52 |
| Intra-mask Baffling Screen | 55 |
| Intra-mask Outer Surface | 57 |
| Inhaled Fresh Air | 60 |
| Blower Air | 65 |
| Patient Exhaled Breath | 70 |
| Screen Curved Internal Wall | 75 |
| Cover | 80 |
| Dome/cover | 90 |
| Dome/cover shell | 95 |
| Dome/cover liner | 100 |
| Wall Vanes | 105 |
| Irregular-Shaped Edge | 110 |
| Curved Vanes | 115 |
| Domed Chamber | 120 |

Sound should be considered during the different valve states associated with breathing: the inspiration, expiration, and apnea states.

Inspiration Sound Considerations:

During inspiration, air enters the mask from the blower. This would be a corresponding sound of the pressurized air from the blower passing into the mask. The airflow rates of the blower air are dependent on the following factors, including the inspiration rate of the user. An average inspiration rate is 15 [breaths/min] at a volume of 500 [cc/breath]. This results in a peak flow of 25 [l/min]. However, this flow rate is parabolic. There is no inspiratory flow just prior to inspiration. During inspiration, it increases to the peak rate, then decreases to zero at the end of the inspiration. So the sound profile of the air entering the mask from the blower is variable due to the parabolic nature of the intake breath. Also, a user can intentionally or unintentionally breathe at a nearly unlimited variability of inspiration patterns. Further, the blower air generates more noise given that the mask may have an open communication path from the inside of the mask to the room. Also, the sound of air entering the mask from the blower is variable and dependent on the blower setting. The sound of the air generated by the blower will depend on the blower setting and rate. Assuming higher velocity flow has a louder sound, the blower air sound will increase as the blower is set to higher settings. To summarize, the inspiration sound considerations include:

1) Blower air with inspiration valves closed (lower inspiration rates/beginning of inspiration);
2) Blower air with inspiration valves open (higher inspiration rates/middle portion of inspiration, where the rate is higher); and
3) Entrained room air passing through the open inspiration valves (both the sound of air entering the mask through the inspiration valves AND the transmission of blower air sound that may exit out of the open inspiration valves).

Expiration Sound Considerations:

During expiration, the inside of the mask is at a pressure above atmospheric pressure. The inspiration valves are maintained closed throughout the expiration. Additionally, the mask design described below maintains expiration pressure slightly above the blower pressure; therefore, the blower path is maintained shut during expiration, and there is no sound of blower air entering the mask. So during expiration, the only anticipated sound from airflow should be the exhaled breath passing through the expiration valve. This sound is dependent on the user's flow rate. For the sinusoidal expected breath described above, this would be a exhalation rate of zero just prior to exhalation that then increases to a peak flow rate of 25 [l/min] at the midpoint of exhalation that then decreases to zero as the exhalation finishes.

Apnea Sound Considerations:

The final breathing state is when the user has a pause in breath (dwell time between inhalation and exhalation) or when an obstructive event occurs. The mask design described below is intended to maintain intra-mask pressure during such a time. Both inspiration and expiration valves are intended to be shut during this state of breathing. Therefore, there should be no flow entering or exiting the mask at this time. This should correspond to a period of particular quiet in the mask function. There may be sound from two possible sources, however:

1) The mask may have an unintended leak through either inspiration or expiration valves coupled with an equivalent amount of air entering from the blower to compensate for the un-intended leak.
2) There may be a leak from a poor fitting or poorly positioned mask. Air could be leaking past the user's nasal interface. This type of leak is best addressed by developing a nasal interface to best fit the majority of users and a support/position head strap that robustly holds the mask in position during use.

In the mask design described below, the noise from such leaks is greatly reduced compared to conventional CPAP due to the system operating at significantly reduced flow rates. The lower the flow rate, the less the sound from leaking.

Figure 1B:
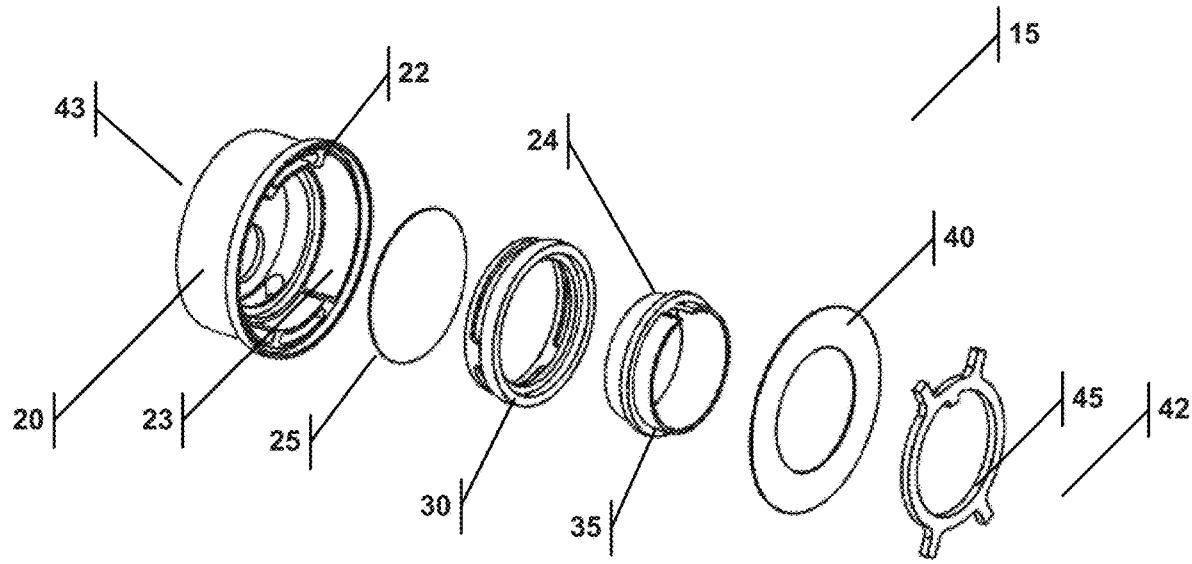
FIG. 1B illustrates in an exploded view the various parts of the novel valve structure of FIG. 1A.
Figure 1F:
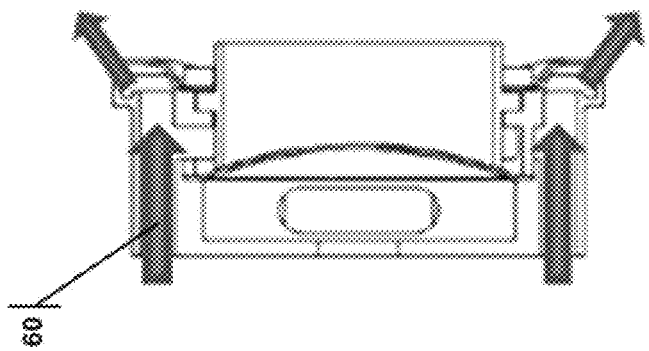
FIG. 1F shows the fresh air flow of the novel valve structure of FIG. 1A during inspiration.
Figure 1E:
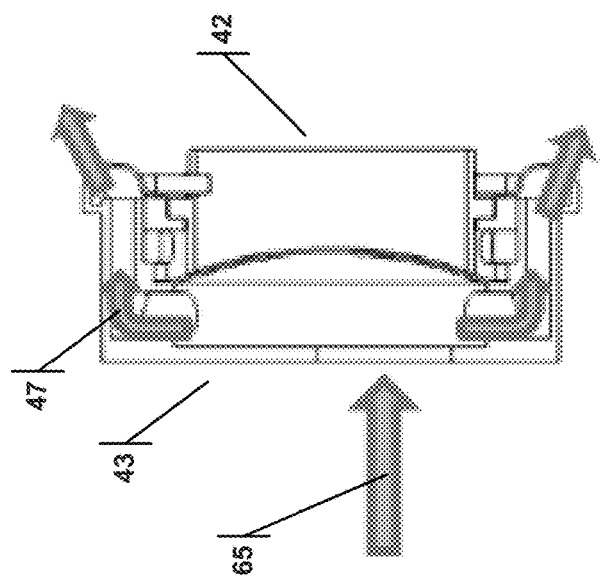
FIG. 1E shows the blower air flow of the novel valve structure of FIG. 1A during inspiration.
Figure 1C:
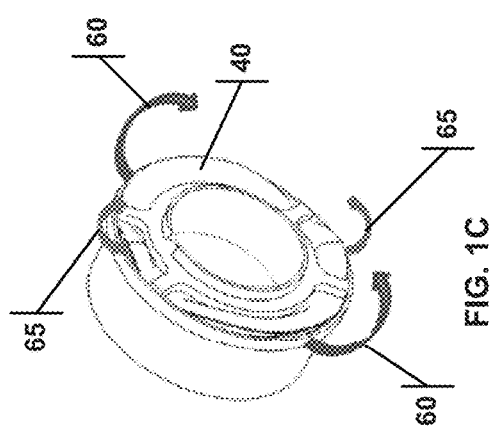
FIG. 1C shows the fresh air flow and the blower air flow of the novel valve structure of FIG. 1A during inspiration.
Figure 1D:
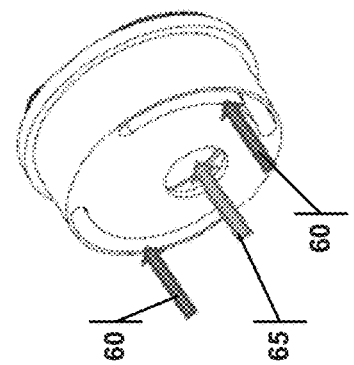
FIG. 1D shows the fresh air flow and the blower air flow of the novel valve structure of FIG. 1A during inspiration.
Figure 1J:
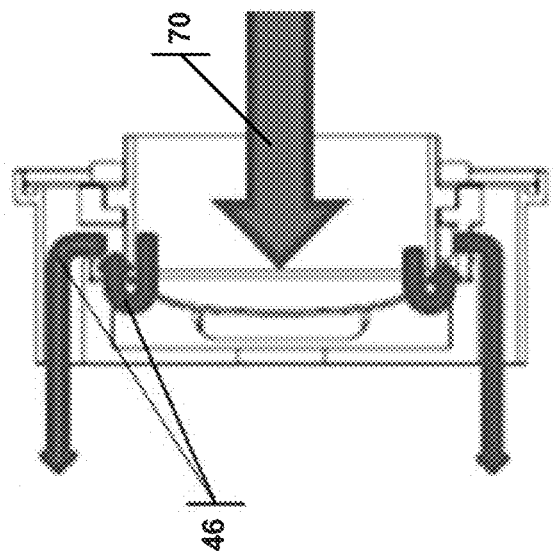
FIG. 1J shows the exhaled breath air flow of the novel valve structure of FIG. 1A during expiration.
Figure 1I:
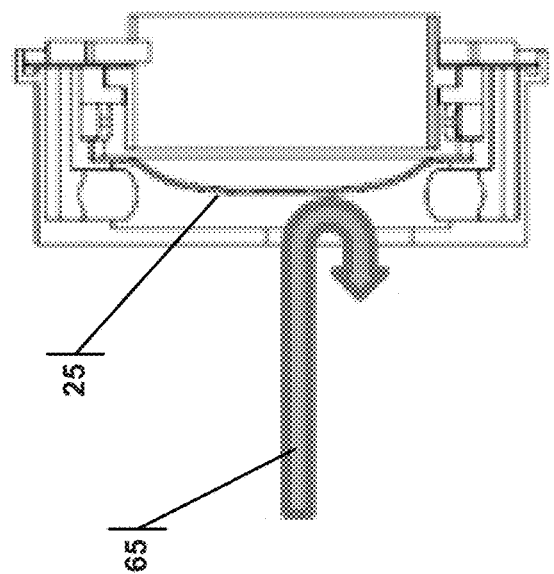
FIG. 1I shows the blower air flow of the novel valve structure of FIG. 1A during expiration.
Figure 1G:
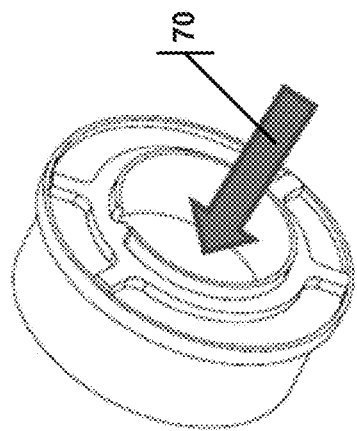
FIG. 1G shows the exhaled breath air flow of the novel valve structure of FIG. 1A during expiration.
Figure 1H:
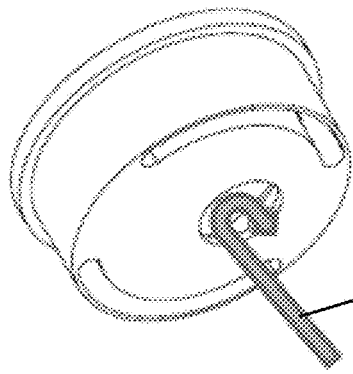
FIG. 1H shows the blower air flow of the novel valve structure of FIG. 1A during expiration.

Co-pending U.S. application Ser. No. 15/334,243 claiming priority to U.S. application 62/311,804 discloses a unique valve as shown in FIGS. 1A and 1B. The sleep mask 10 contains a sleep mask valve structure 15 that is comprised of a rigid or semi-rigid valve housing 20 that further includes an expiratory valve retaining seat 30, an inspiratory valve retailing seat 35, and a retaining clip 45. The inspiratory and expiratory valves further include an expiratory valve membrane 25 and an inspiratory valve membrane 40, each of which may be formed from a sound absorbing material, such as an elastomer. To further mitigate sound, the valve housing 20 may include a sound absorbing liner 23, made of a material with a preferred durometer of 5 A to 90 A.

The valve housing 20 also forms an air conduit outlet 21, and an inspiratory valve seat 22, that in combination with the inspiratory valve membrane 40 creates a one-way valve. The valve housing 20, through the expiratory valve retaining seat 30 forms an expiratory valve seat 24 that forms variable resistance expiratory valve, that can be adjusted based on the pressure of the blower air. Unlike the prior art, the supplied air and the valve controlling air may be combined into a single hose with a single lumen. This has unique advantages, in that the hose can be smaller, more supple (an important user feature is not having a cumbersome hose to distract from sleeping), easier to clean (the system need not have any elongated, small lumens that end in a closed compartment in the valve resistance generating chamber), and easier to connect as only a single orientation independent hub is needed at either end. The sleep mask valve structure 15 has an intra-mask side 42 that is proximal (as a function of air path) to the patient and an outside mask side 43 that is distal to the patient.

The operation of this sleep mask valve structure 15 is shown in FIGS. 1C-1L. Specifically, FIGS. 1C-1F illustrate the inspiration mode and, in particular, the flow paths of the inhaled fresh air 60 and the blower air 65. The fresh air 60 moves past the inspiratory membrane 40, and as does the blower air 65 (see FIG. 1C). The valve structure 15 and housing 20, therefore, define inspiratory airflow conduit (shown by the airflow movement arrows in FIGS. 1C-1F) accommodating airflow from the outside mask side 43 to the intra-mask side 42. The inspiratory airflow conduit has a tortuous path with at least one change of direction 47 that is greater than or equal to 75 degrees.

FIG. 1G-1J illustrates the expiration mode and the flow paths of the blower air 65 and the patient's exhaled breath 70. In the expiration mode the blower air 65 applies a pressure against the expiratory valve membrane 25 (the "J" shape of the blower air 65 arrow is intended to represent the blower air 65 being impeded at the expiratory valve membrane 25 and is not intended to represent a change of direction or a return towards the blower). This resistance can assist in preventing an apnea event. The valve structure 15 and housing 20 therefore define expiratory airflow conduit (shown by the exhaled breath 70 in FIGS. 1G-1J) accommodating airflow from the intra-mask side 42 to the outside mask side 43. The expiratory airflow conduit has a tortuous path with at least two changes of direction 47, each of which is greater than or equal to 75 degrees.

Figure 1L:
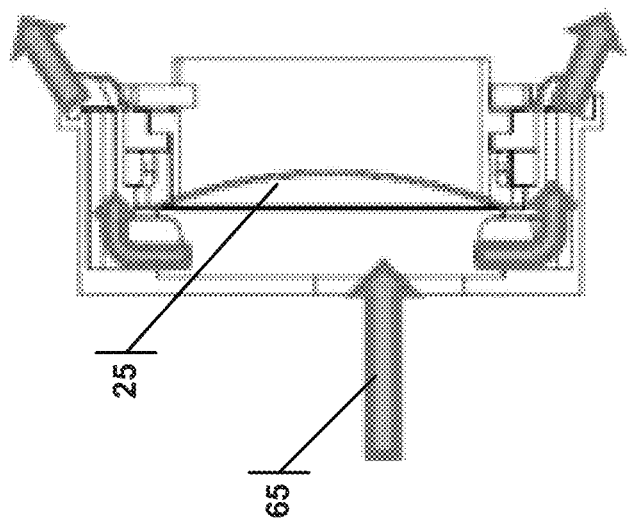
FIG. 1L shows the blower air flow of the novel valve structure of FIG. 1A during apnea.
Figure 1K:
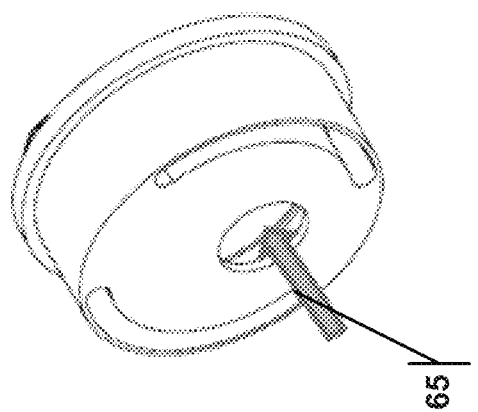
FIG. 1K shows the blower air flow of the novel valve structure of FIG. 1A during apnea.

Finally, FIGS. 1K-1L illustrate the apnea mode of the valve structure, with the blower air 65 applying a pressure against the expiratory valve membrane 25 while simultaneously providing a positive pressure of air to the patient, thus offering a therapeutic pneumatic splint that maintains the patient's airway open preventing an apnea event.

Figure 2:
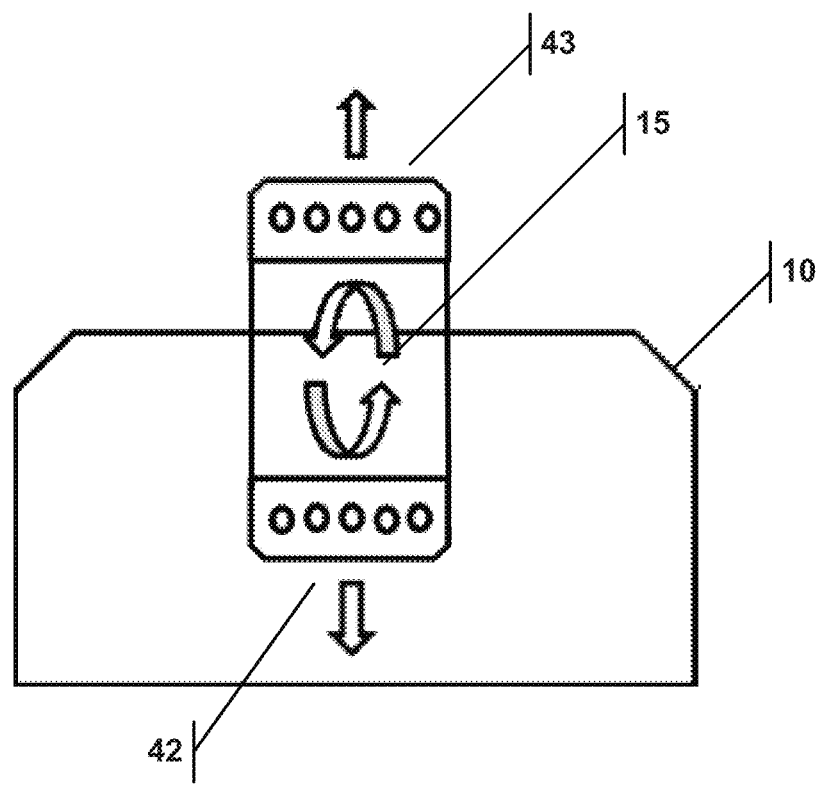
FIG. 2 is a diagram showing possible positions of sound mitigating structures.

The structures and methods described herein can to provide sound mitigation features on both the sides of the valve structure: The inwardly facing intra-mask side 42 and the externally outside-mask side 43, as shown in FIG. 2. In addition, sound mitigations structures and methods are disclosed that can implemented within the sleep mask valve structure 15 itself.

Figure 3A:
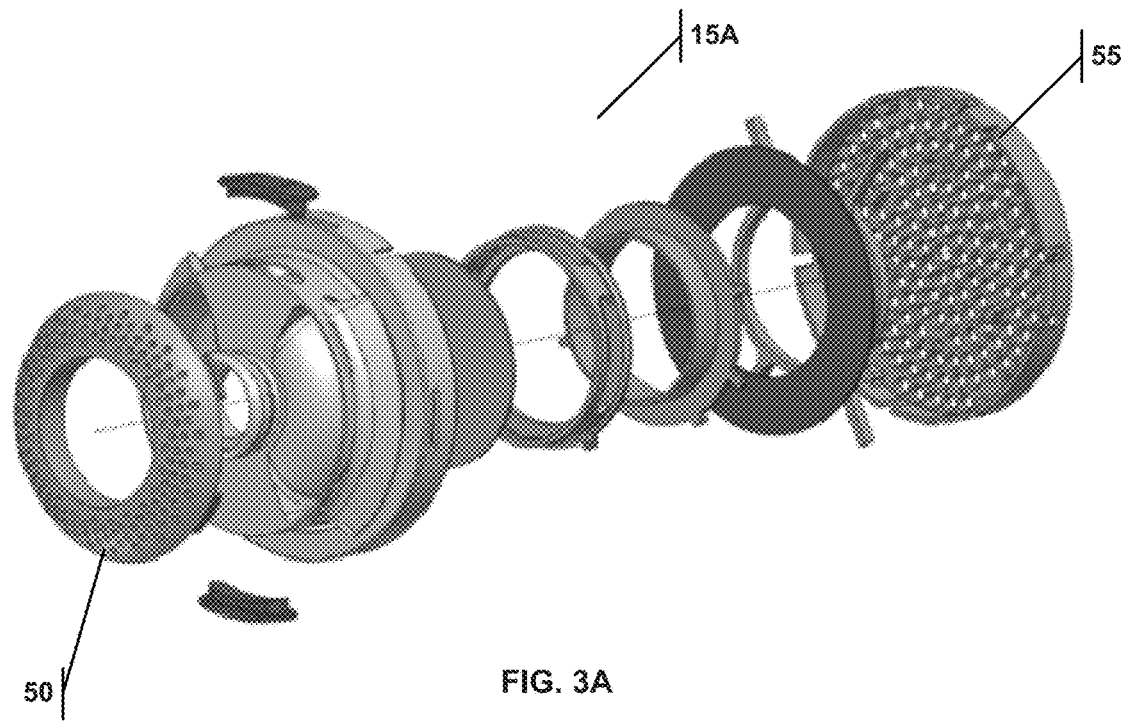
FIG. 3A is an improvement on the design of FIG. 1A, including baffling screens.
Figure 3B:
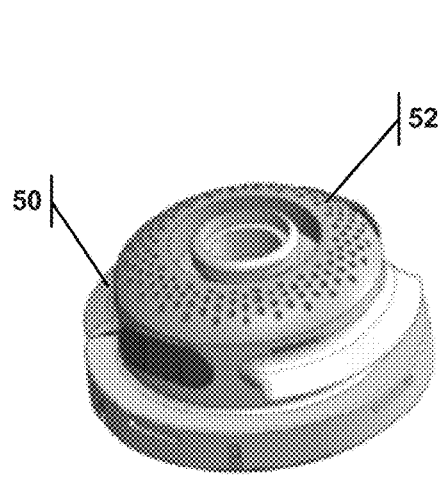
FIG. 3B is another view of the design of FIG. 3A.
Figure 3C:
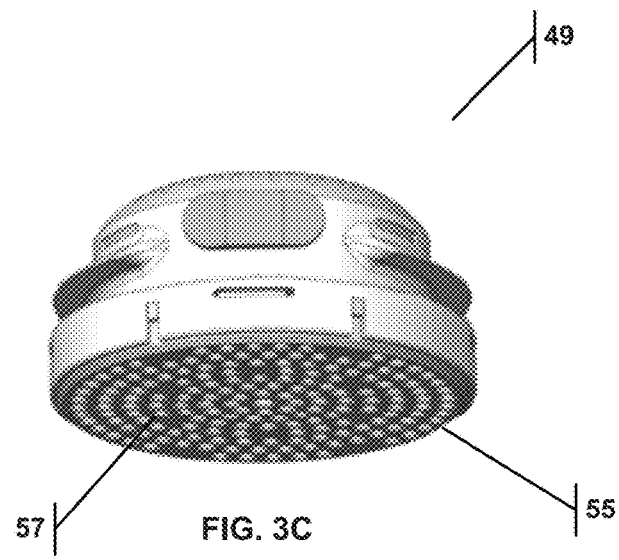
FIG. 3C is another view of the design of FIG. 3A.

FIGS. 3A-3C show an improved design of the sleep mask valve structure 15A that includes an outer mask baffling screen 50 with an outer surface 52 with a plurality of opening that allows airflow across the screen 50. Similarly, the valve structure 15A may further include an intra mask baffling screen 55 with an intra-mask outer surface 57 with a plurality of openings that allows airflow across the screen 55. The entire valve structure 15A can constructed as a cartridge 49 that can be easily inserted into a nasal pillow, mask, or other pliable structure that seals against the patient's nose and/or mouth.

The sound mitigating screens shown use an array of small holes or slots. It would be desirable for any fenestrated baffle screen to provide as little resistance as possible while maintaining coverage over the entire flow path. In a preferred embodiment, the resistance (measured as a pressure drop) across the cover at a flow rate of 25 [l/min] is less than 0.5[cm H2O]. In order to provide maximum coverage and minimal resistance, careful consideration must be given to the geometry of any given hole or slot in the screen. These fenestrations should have tapers on both sides with a preferred taper of 45 +/−15 degrees on each vent hole. Additionally, material thickness (hole/slot depth) should be minimized, and it would be preferable that the depth is no more than 0.050 [in].

It is further preferred that the pattern be constructed with as small of a hole diameter as practical and with as dense of pattern to fit the surface applied to. It is also preferable that the total hole area is equal to or larger than the adjacent flow path leading to it. It is preferable that the hole size be between 0.01[in] and 0.05[in] in diameter. Using too small of a diameter could entrap foreign matter (dirt) easily, and would be difficult to clean.

The fenestrated screens may also preferably have a hole/slot pattern consisting of multiple diameters intermixed across the vent surface. This mixing of multiple sizes has a benefit of changing the synchronization of the soundwaves so that they are out of phase. By doing this, sound will be diminished, since sound waves will not be exiting synchronized and additive.

Figure 4A:
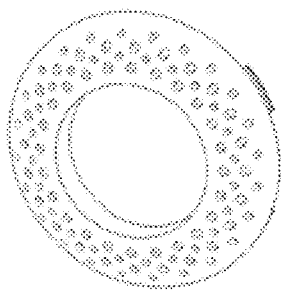
FIG. 4A is a first embodiment of the outer mask baffling screen.
Figure 4A:
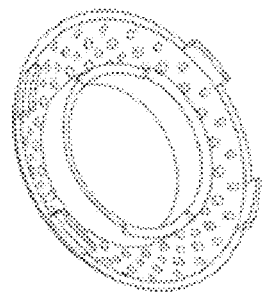

Various screen patterns are presented in FIGS. 4A-4FF, specifically:

FIGS. 4A and 4AA illustrate a pattern of holes that allow air to pass while reflecting sound back into the valve structure. The hole pattern has variable orifice sizes and is on a curved surface that adds geometric variability to confound and trap soundwaves.

Figure 4B:
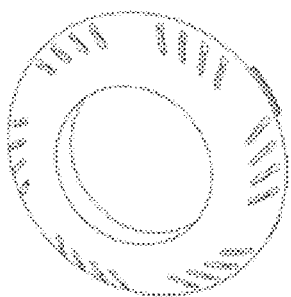
FIG. 4B is a second embodiment of the outer mask baffling screen.
Figure 4B:
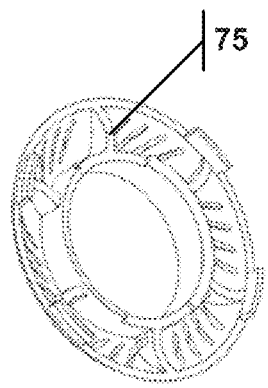

FIGS. 4B and 4BB illustrate a pattern of slots that allows air to pass while reflecting sound back into the valve structure. The slot pattern is angled and on a curved surface, which adds geometric variability to confound and trap soundwaves. This embodiment also has a curved internal wall 75 radiating from the center of the screen to compartmentalize, reflect, and confound sound waves.

Figure 4C:
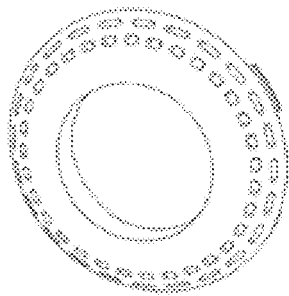
FIG. 4C is a third embodiment of the outer mask baffling screen.
Figure 4C:
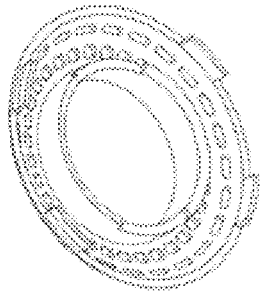

FIGS. 4C and 4CC illustrate a pattern of slots that allows air to pass while reflecting sound back into the valve structure. The slot pattern is of two sizes and is perpendicular to a curved surface, which adds geometric variability to confound and trap soundwaves.

Figure 4D:
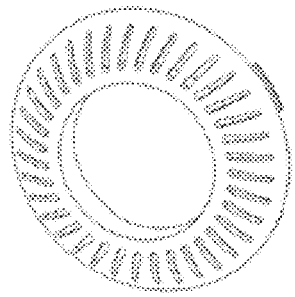
FIG. 4D is a fourth embodiment of the outer mask baffling screen.
Figure 4D:
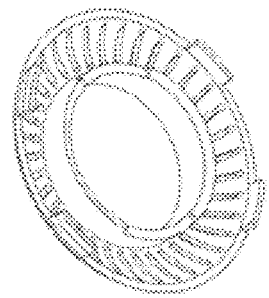

FIGS. 4D and 4DD illustrate a pattern of slots that allow air to pass while reflecting sound back into the valve structure. The slot pattern is angled, variable in width per slot and on a curved surface that adds geometric variability to confound and trap soundwaves.

Figure 4E:
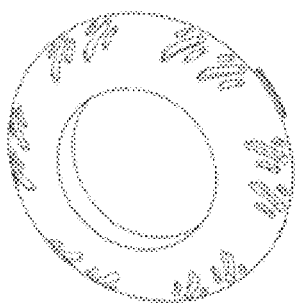
FIG. 4E is a fifth embodiment of the outer mask baffling screen.
Figure 4E:
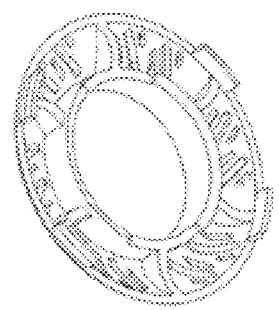

FIGS. 4E and 4EE illustrate pattern of slots that allows air to pass while reflecting sound back into the valve structure. The slot pattern is angled and on a curved surface, which adds geometric variability to confound and trap soundwaves. The slot length is variable to further enhance geometric variability to mitigate sound propagation. This embodiment also has a curved internal wall to compartmentalize, reflect, and confound soundwaves.

Figure 4F:
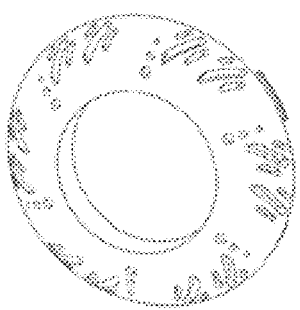
FIG. 4F is a sixth embodiment of the outer mask baffling screen.
Figure 4F:
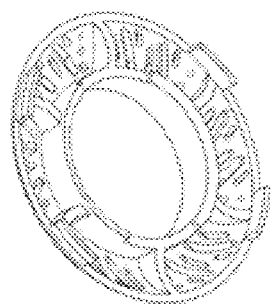

FIGS. 4F and 4FF illustrate a pattern of slots and holes that allows air to pass while reflecting sound back into the valve structure. The slot and hole pattern is angled and on a curved surface, which adds geometric variability to confound and trap soundwaves. The slot length is variable along with the holes of various orifice sizes to further enhance geometric variability to mitigate sound propagation. This embodiment also has a curved internal wall to compartmentalize, reflect, and confound soundwaves.

Figure 4G:
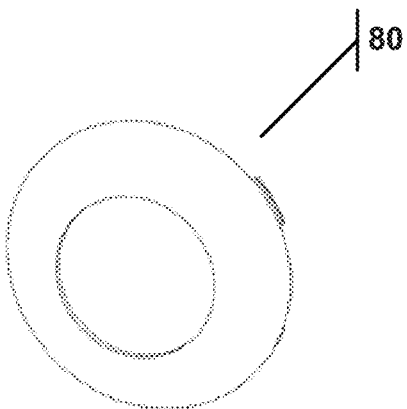
FIG. 4G is a seventh embodiment of the outer mask baffling screen.
Figure 4G:
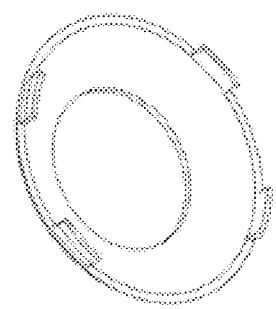
Figure 5:
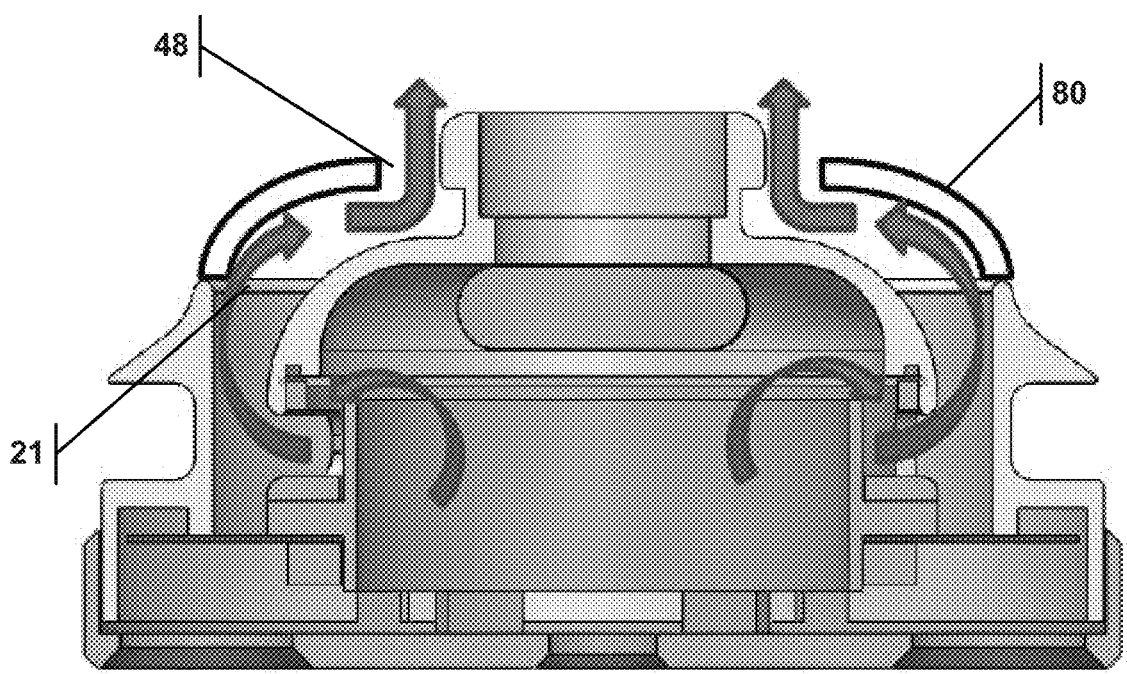
FIG. 5 illustrates the tortuous air flow path of the novel valve structure of FIG. 3A for an exhaled breath, when a cover of FIG. 4G is used.

FIGS. 4G and 4GG illustrate a configuration that is different from the previous embodiments. It is a sound mitigating cover 80 that does not have the vent features cut through the dome of the cap. Instead, the screen enhances the tortuous path of the air flow. As air exits out the valve structure at outlet 21 (FIG. 5), it is bent along the curved inner wall of cover 80 and directed towards the center orifice. Ultimately, the cover 80 adds an additional change of direction to the air flow path, as shown in FIG. 5. This tortuous path internally reflects the soundwaves and mitigates noise. It should also be noted that the expiratory airflow conduit and inspiratory conduit path share at least one change of direction 48.

The hole and slot patterns just discussed with references to the outer mask baffling screen (i.e., FIGS. 4A-4GG) may also be applied to the intra-mask baffling structure. Further, the openings can be of various shapes other than the circular and elongate slots depicted in the figures.

Figure 6:
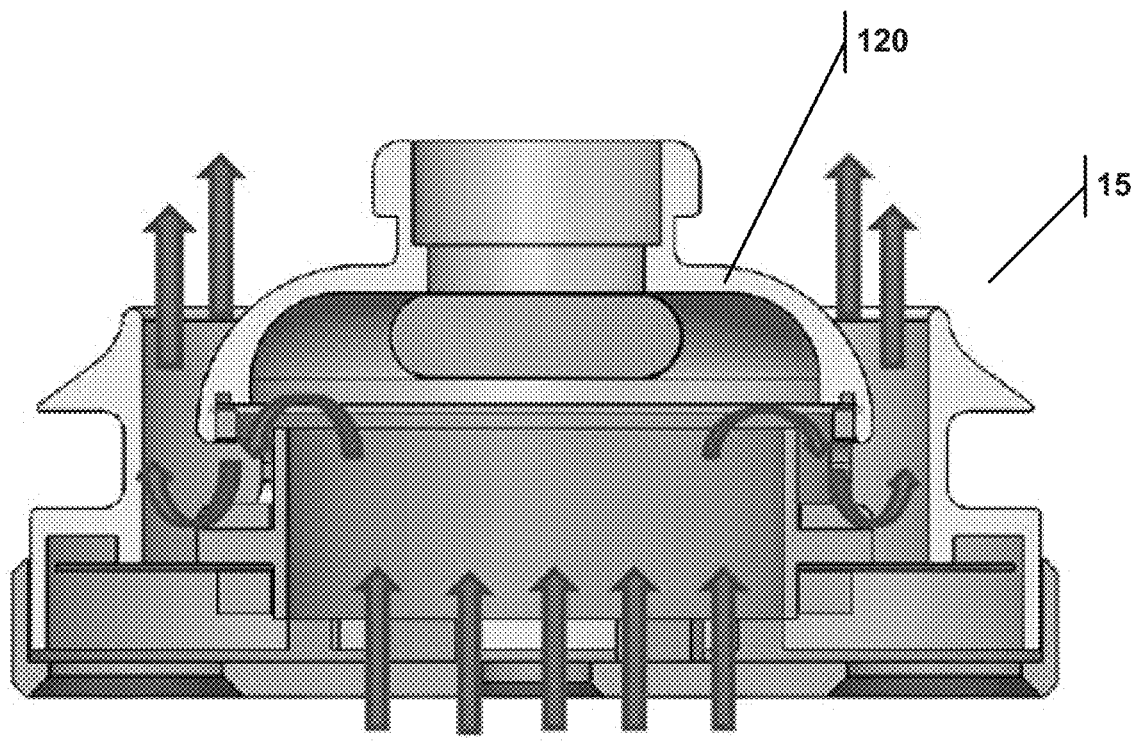
FIG. 6 illustrates the tortuous air flow path of the novel valve structure of FIG. 3A for an exhaled breath, when no cover or screen is used.
Figure 7:
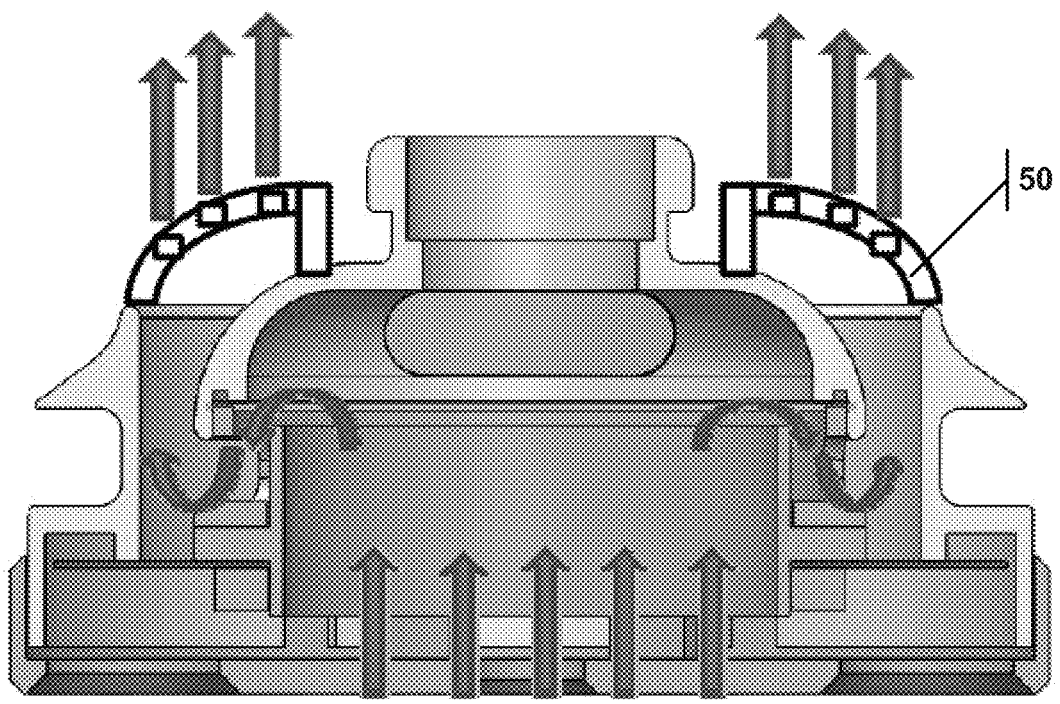
FIG. 7 illustrates the tortuous air flow path of the novel valve structure of FIG. 3A for an exhaled breath, when a baffle screen is used.

In addition to these screens, the design of the internal flow path can be used to mitigate sound. The flow path should be tortuous such that the sound of the air flow can be internally reflected. FIG. 6. Illustrates such a tortuous path that requires the exhaled air to take at least two 180-degree turns before exiting the sleep mask valve structure 15. It is these turns that cause the sound to become internally reflected and mitigated. The additional of an outer mask baffling screen 50 shown in FIG. 7 further mitigates noise. It is preferable that the surface of the dome chamber 120 be curved where possible to additionally mitigate noise. Curved surfaces reduce the ability of the structure to transmit noise.

Figure 8A:
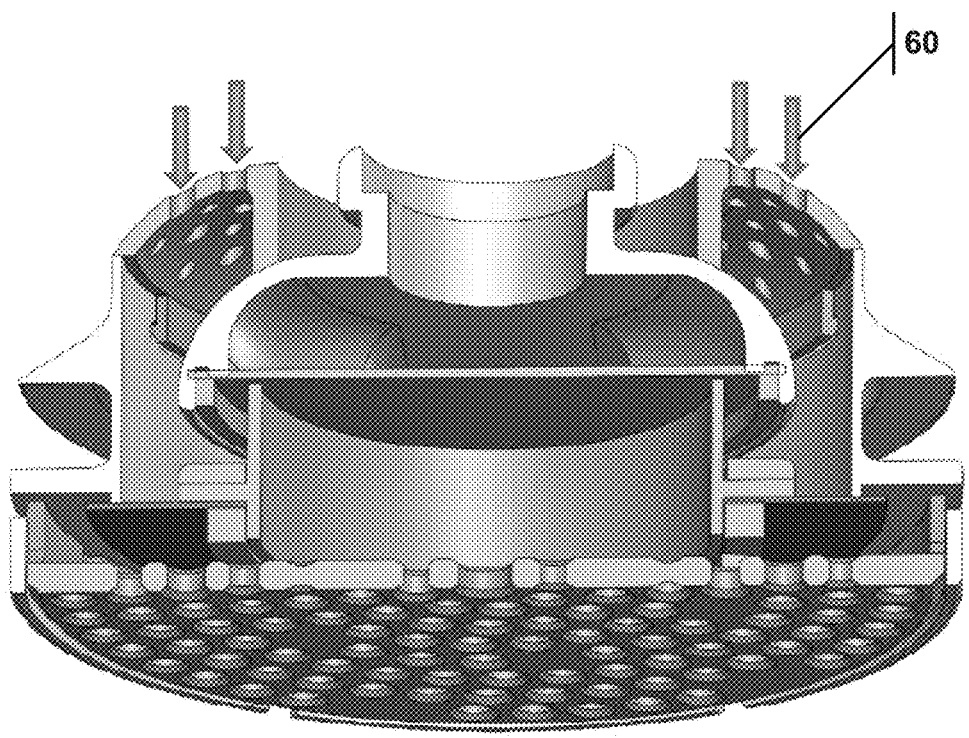
FIG. 8A illustrates the tortuous air flow path of the novel valve structure of FIG. 3A for inhaled fresh air, when a baffle screen is used.
Figure 8B:
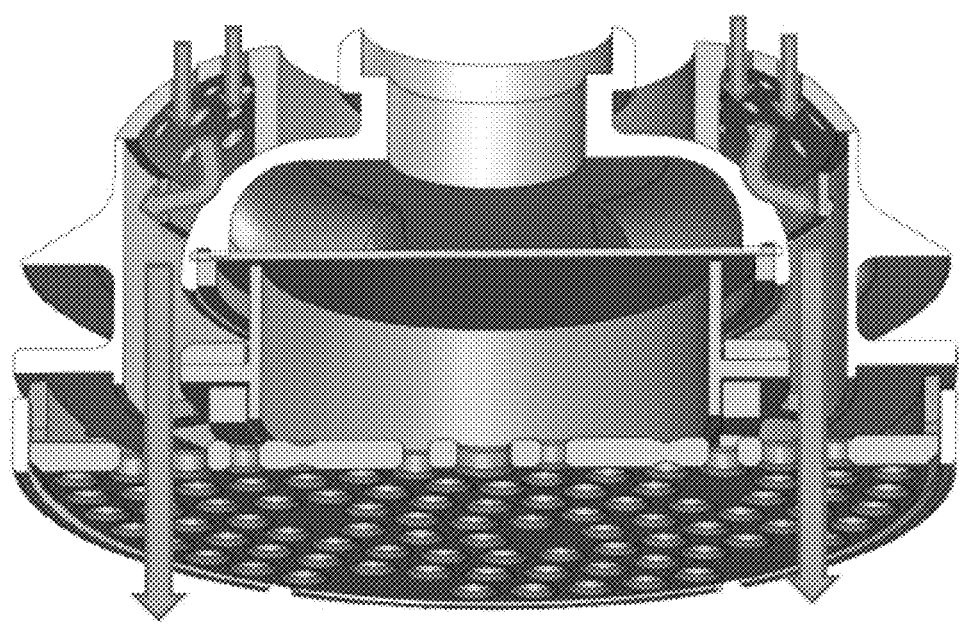
FIG. 8B illustrates the tortuous air flow path of the novel valve structure of FIG. 3A for inhaled fresh air, when a baffle screen is used.

FIGS. 8A and 8B illustrate the tortuous path that inhaled fresh air 60 must take. Again, there is an abrupt turn that internally reflects sound waves. It should further be noted that the inspiratory membrane 40 in FIG. 8B has been removed to more clearly show the tortuous path. The inclusion of this membrane would actually add further variability to the tortuous path as the airflow negotiates around the membrane, and enhances the sound mitigation properties (this additional variability is shown in detail in FIG. 1C). And because the inspiratory membrane 40 is made of an elastomer, it also acts as a sound absorption structure.

Figure 9:
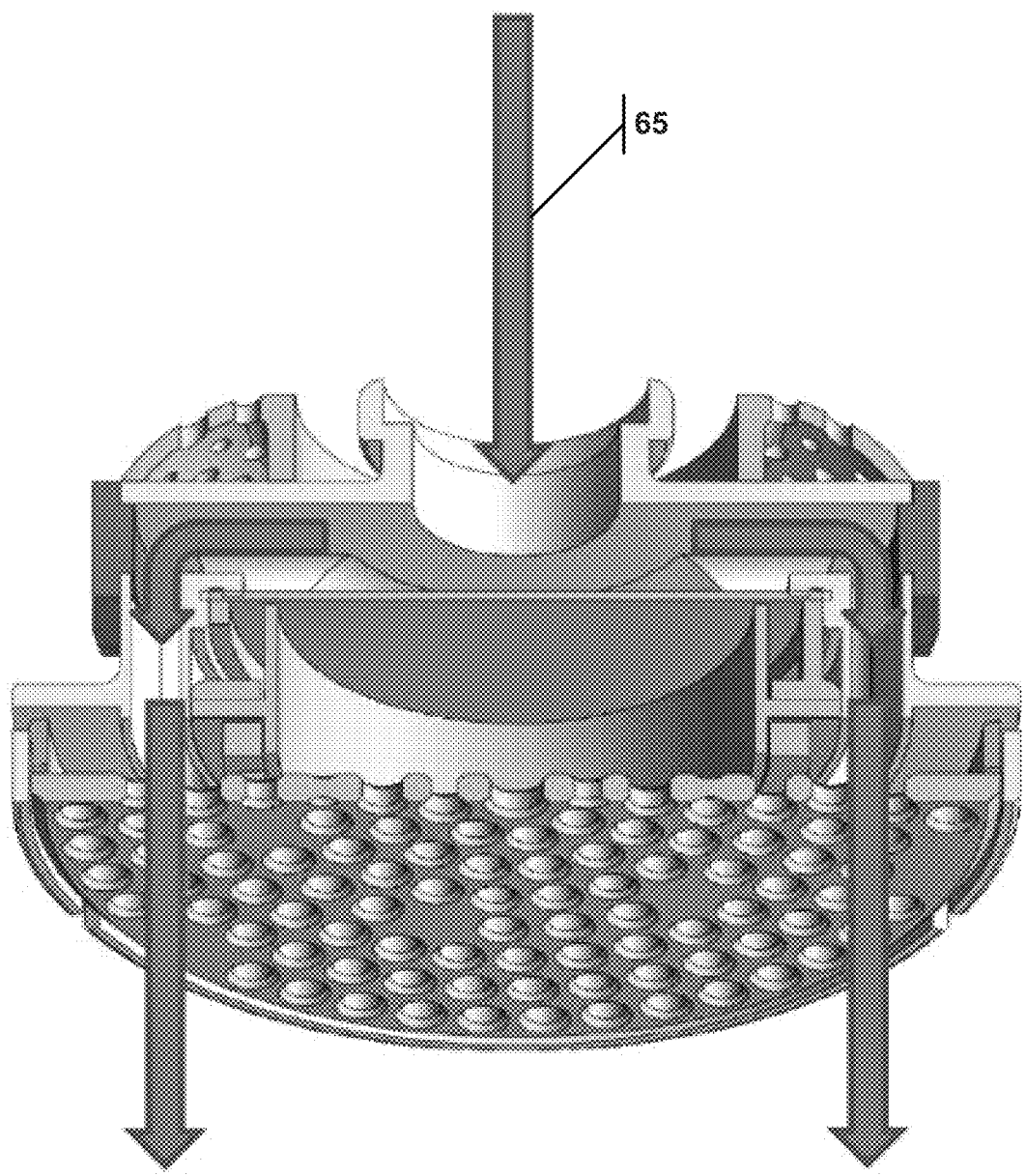
FIG. 9 illustrates the tortuous air flow path of the novel valve structure of FIG. 3A for blower air, when a baffle screen is used.

FIG. 9 illustrates the tortuous path that blower air blower air 65 must take. Again there is an abrupt turn that internally reflects wound waves. It should further be noted that the inspiratory membrane 40 in FIG. 9 has been removed to more clearly show the tortuous path. The inclusion of this membrane would actually add further variability to the tortuous path as the airflow negotiates around the membrane, and enhances the sound mitigation properties.

Figure 10A:
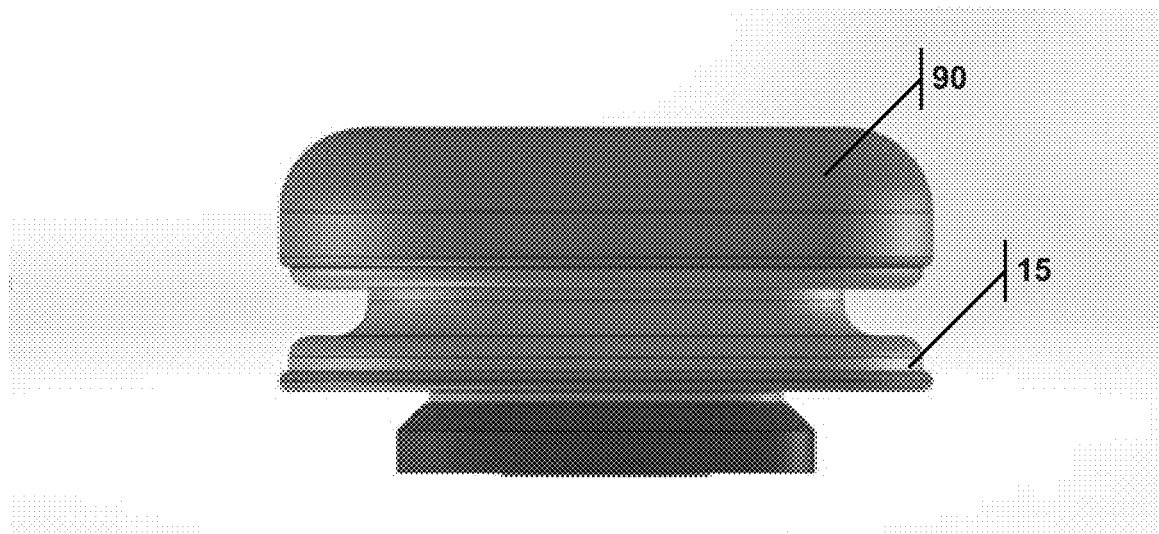
FIG. 10A illustrates a dome/cover to mitigate sound.
Figure 10B:
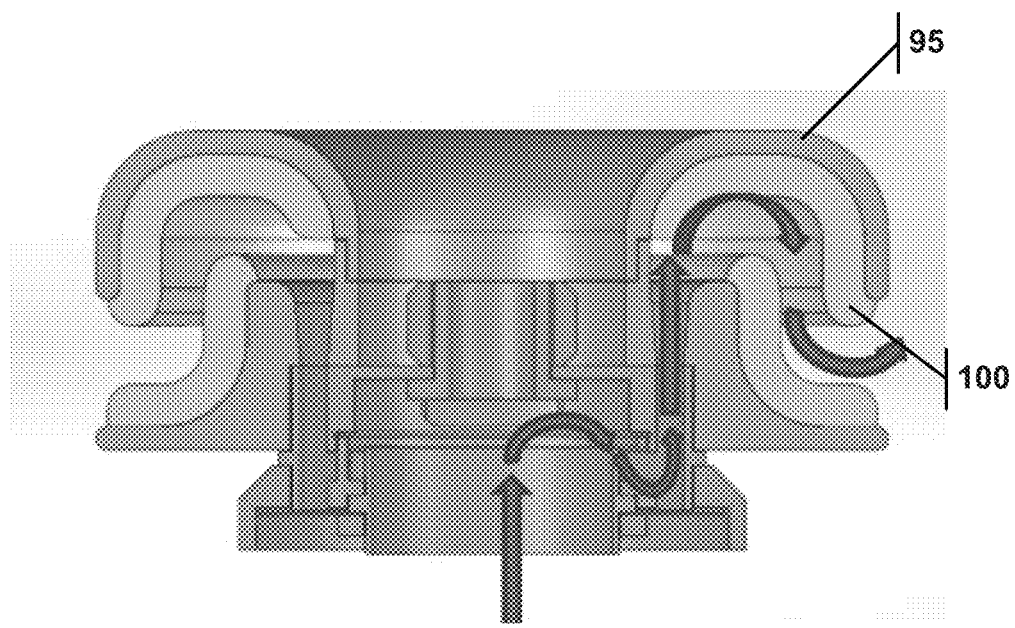
FIG. 10B is a cross section of the dome/cover of FIG. 10A.

FIGS. 10A and 10B illustrate a dome/cover 90 that can be installed on the outside mask side of the valve structure and introduces additional turns to the air flow tortuous path. Specifically, as shown in FIG. 10B, the exhaled breath 70 must not only negotiate the two 180-degree turns within the valve structure, but the dome/cover 90 introduces another two such turns. The dome/cover 90 consists of a rigid/semi-rigid shell 95 lined with a sound absorbing material 100. The rigid shell 95 can be fabricated from metal such as stainless steel or, more preferably, a plastic such as polycarbonate or ABS. Additionally the shell 95 could be semi rigid and made from a material such as silicone or urethane with a preferred durometer of 50 A to 90 A. A benefit of a semi-rigid shell 95 is it would provide additional sound absorption in that it would be less prone to vibrating or acting as a transmitter. The liner 100 could be a soft elastomer, such as silicone with a durometer of 40 A or less. Additionally, the liner 100 could be fabricated from an open or closed cell foam, preferably an open-celled silicone foam. More preferably, it is an ultra-soft foam with a density of 12 [lbs./ft^3] and a pressure to compress 25% of 4 [psi].

The shell 95 and sound absorbing liner 100 create a tortuous "S" shaped path out of the valve structure 15. The tortuous path is a desirable sound mitigating feature because it prevents soundwaves from having a straight path out of the valve structure 15. This has a benefit of reflecting some soundwaves back into the valve structure 15. Additionally, the sound absorbing liner 100 can capture sound waves as they reflect along the tortuous path. Lastly, this configuration has a diffuse geometry in that as the air flow exits from the central diameter, it travels to an annular exit that is on a bigger diameter, hence allowing the cross section of the vent flow path to increase as the air flow travels outbound. Diffusion is beneficial because as a given flow rate travels from a smaller total flow path to a larger total flow path, conservation of mass dictates that flow velocity must decrease, and lower velocity flow inherently produces less sound than higher velocity flow.

Figure 11B:
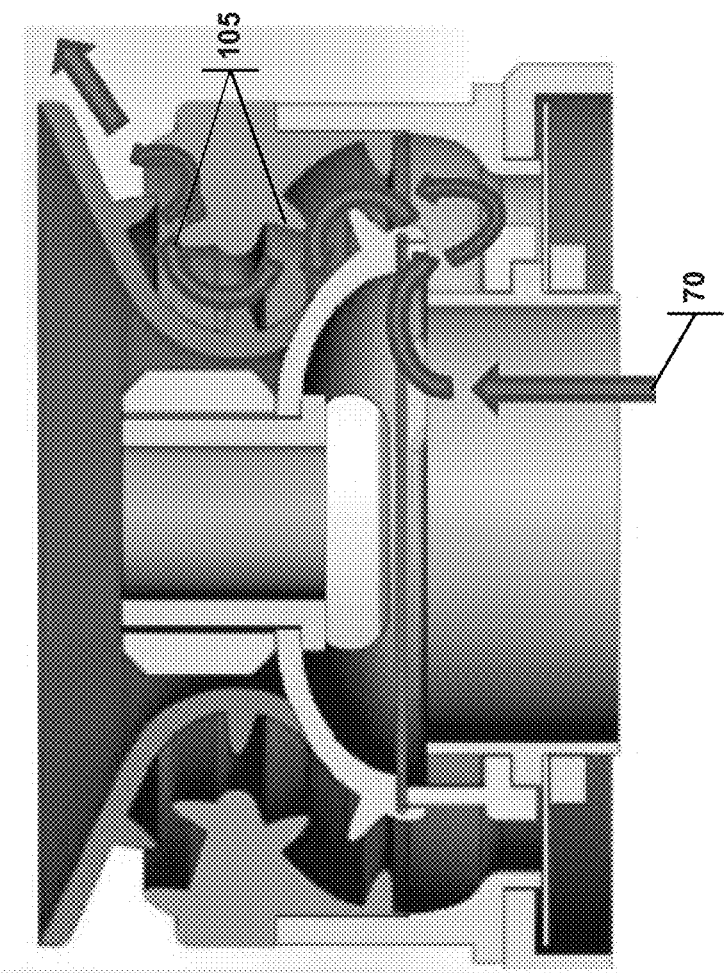
FIG. 11B is a cross section of the dome/cover of FIG. 11A.
Figure 11A:
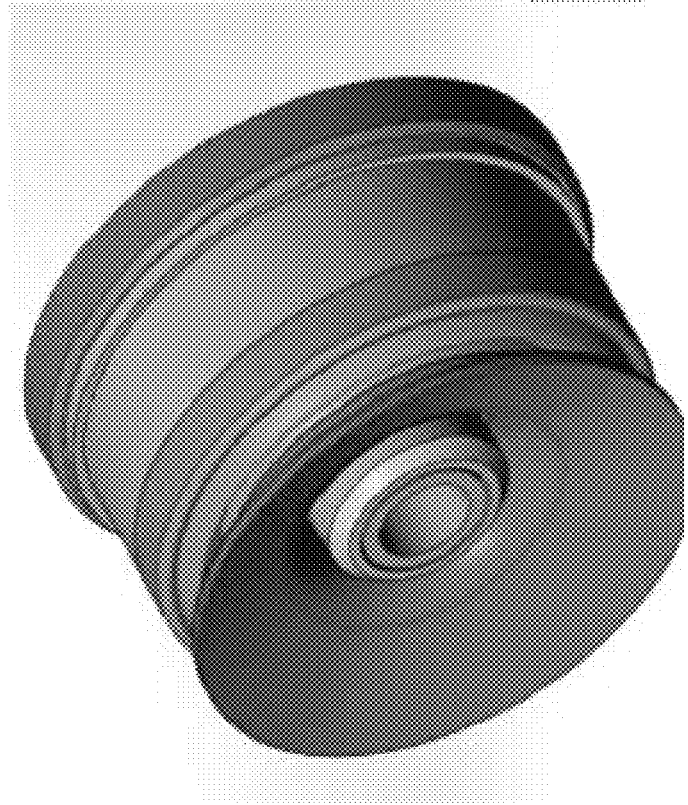
FIG. 11A illustrates wall vanes to mitigate sound.

A tortuous airflow path can be augmented further by the introduction of vanes or baffles within the valve structure 15, as shown in FIGS. 11A and 11B. For example, in FIG. 11B the exhaled breath airflow 70 not only negotiates the two 180-degree turns, but it also must worm around several vanes 105 that further bend the airflow path. The walls defining the tortuous airflow path have been additionally configured with a series of staggered, protruding vanes 105. These vanes provide additional sound reflecting and dissipating surfaces. This embodiment could be made from completely rigid or semi-rigid material. Additionally, it could be configured like the previous embodiment, where the inner surface, including the vanes, is made from a sound-absorbing material, such as open-celled foam.

Figure 12B:
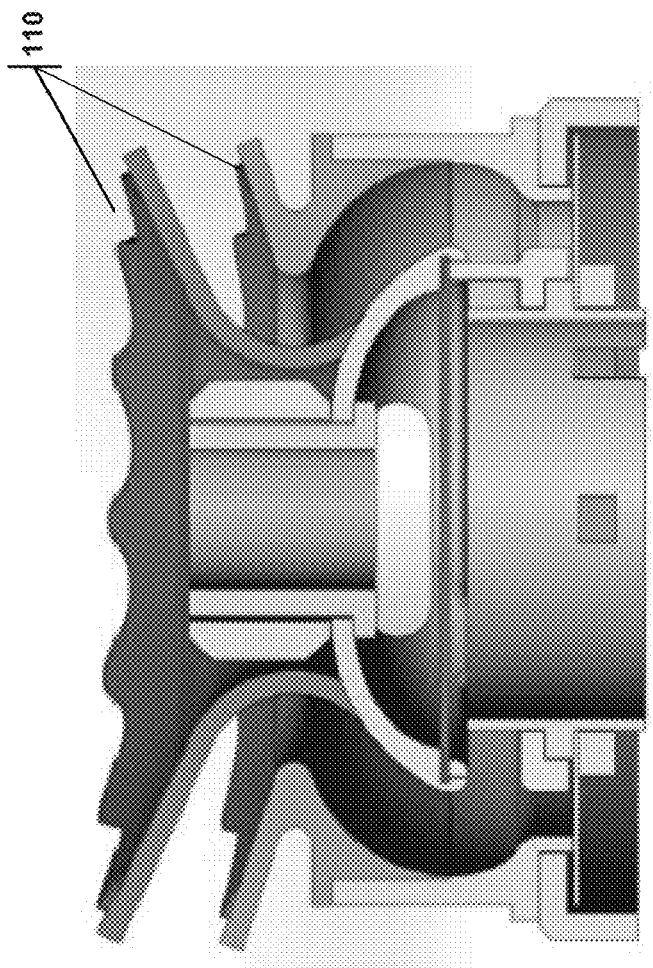
FIG. 12B is a cross section of the dome/cover of FIG. 12A.
Figure 12A:
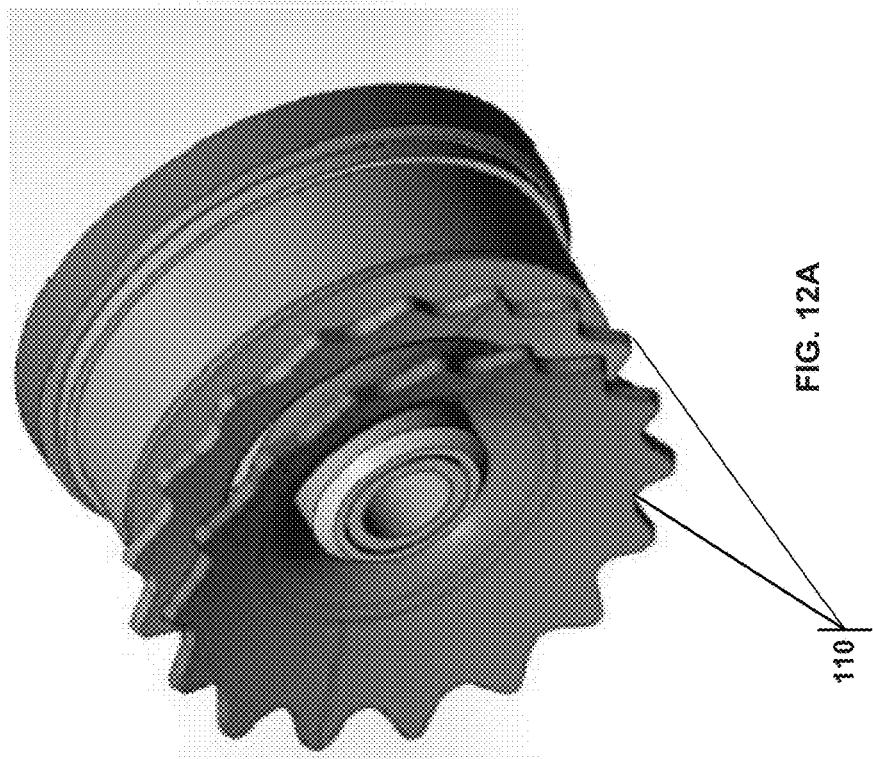
FIG. 12A illustrates irregular edges to mitigate sound.

To further mitigate sound, an irregular set of edges on the airflow outlet may be used to break up the turbulence noise between shear layers. This is shown in FIGS. 12A and 12B. Due to the irregular shape of the edge of the airflow path (shown as a scalloped-shaped edge 110), there are various lengths to any given air flow path. The various path length creates a configuration where there is various travel (dwell times) for sound as it seeks to exit. This has a benefit of changing the synchronization of the soundwaves so that they are out of phase and will not be exiting synchronized and additive.

Figure 13B:
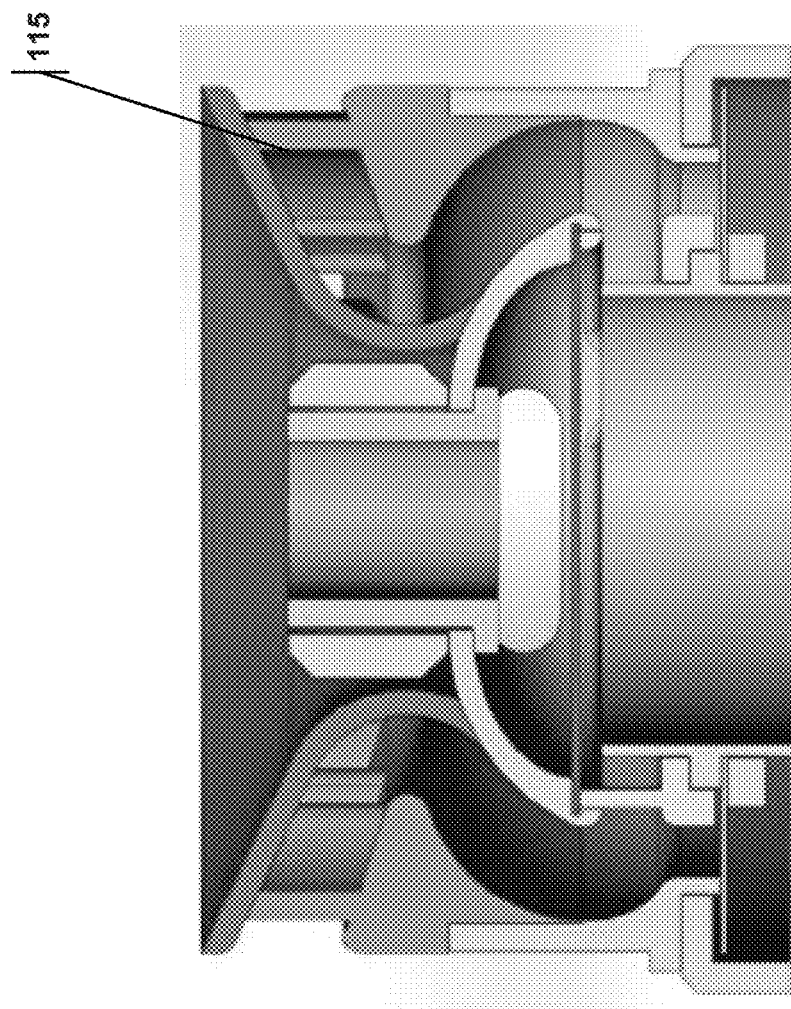
FIG. 13B is a cross section of the dome/cover of FIG. 13A.
Figure 13A:
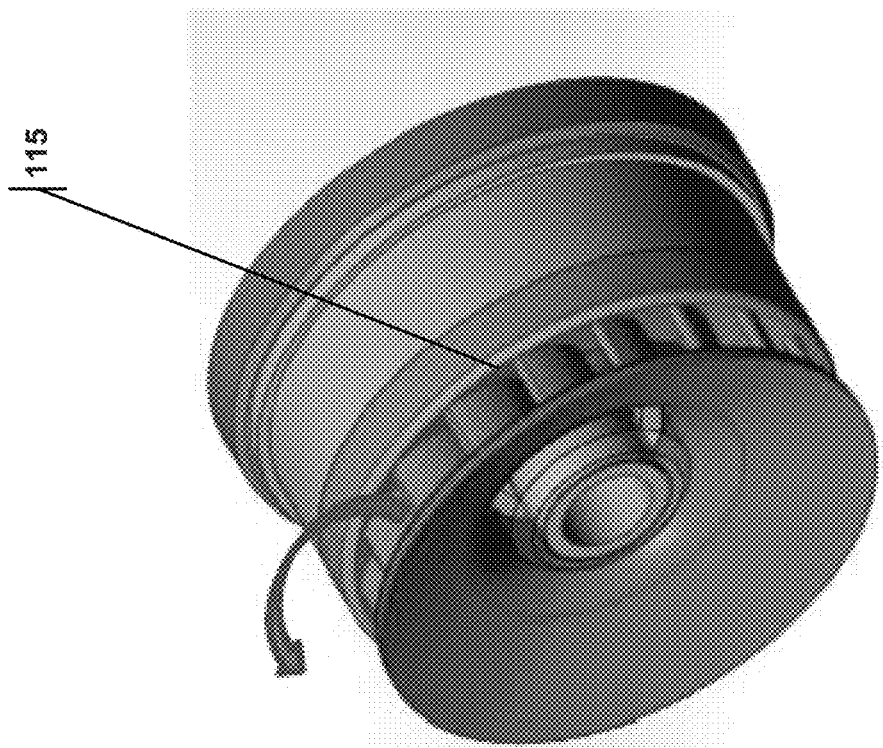
FIG. 13A illustrates curved vanes to mitigate sound.

Another embodiment shown in FIGS. 13A and 13B provides sound mitigating attributes and is an outlet with a series of curved vanes 115 such that the air flow path is not a straight line but configured in a smooth arc to maintain a smooth flow despite the change in direction. Many of the embodiments described allow the air flow within the valve structure or upon exiting the structure to remain in the substantially the same plane. For example, in FIG. 10B, the air stream of the exhaled breath is maintained in substantially in the plane define by the plane of the paper. The curved vanes 115 shown in FIG. 13B change the direction of the air flow out of the plane of the paper. Additionally, the vanes would promote an organization of turbulent flow towards or into laminar flow.

Although exemplary embodiments and applications of the invention have been described herein including as described above and shown in the included example Figures, there is no intention that the invention be limited to these exemplary embodiments and applications or to the manner in which the exemplary embodiments and applications operate or are described herein. Indeed, many variations and modifications to the exemplary embodiments are possible as would be apparent to a person of ordinary skill in the art. The invention may include any device, structure, method, or functionality, as long as the resulting device, system or method falls within the scope of one of the claims that are allowed by the patent office based on this or any related patent application.

The invention claimed is:

1. A sleep mask valve structure for treating a patient suffering from obstructive sleep apnea, the valve structure comprising:
   a rigid valve housing comprising an inspiratory valve and a pneumatically adjustable expiratory valve, the housing further defining an outside mask side, and an intra-mask side, and further defining an expiratory airflow conduit accommodating airflow from the intra-mask side to the outside mask side and an inspiratory airflow conduit accommodating airflow from the outside mask side to the intra-mask side;
   wherein the expiratory airflow conduit comprises at least two changes of direction, with each direction change greater than or equal to 75 degrees;
   wherein the inspiratory airflow conduit comprises at least one change of direction greater than or equal to 75 degrees;
   wherein the expiratory airflow conduit and inspiratory conduit paths share at least one change of direction;
   wherein the valve structure is a removable cartridge adapted to be inserted into a nasal pillow or mask; and
   wherein the expiratory valve is constructed to be fluidly connected to a blower air flow, wherein the expiratory valve is pneumatically adjusted based on the pressure of the blower air flow delivered through a single lumen hose.

2. The valve structure of claim 1, wherein the expiratory airflow conduit comprises a plurality of vanes, wherein the vanes introduce an additional change of direction to the expiratory airflow conduit that is greater than or equal to 75 degrees.

3. The valve structure of claim 2, wherein the plurality of vanes introduces an additional change of direction to the inspiratory airflow conduit that is greater than or equal to 75 degrees.

4. The valve structure of claim 3, wherein the vanes are curved.

5. The valve structure of claim 1, further comprising an outer mask baffling screen.

6. The valve structure of claim 5, wherein the outer mask baffling screen comprises an outer surface with a plurality of openings that allows for airflow across the baffling screen, the plurality has at least two differently sized openings, and the different sized openings are interspersed along the outer surface.

7. The valve structure of claim 6, wherein the openings are circular, elongate or both.

8. The valve structure of claim 1, further comprising an intra-mask baffling screen.

9. The valve structure of claim 8, wherein the intra-mask baffling screen comprises an intra-mask outer surface with a plurality of openings that allows for airflow across the baffling screen, the plurality has at least two differently sized openings, and the differently sized openings are interspersed along the outer surface.

10. The valve structure of claim 9, wherein the openings are circular, elongate or both.

11. The valve structure of claim 1, wherein the valve housing comprises a sound absorbing liner.

12. The valve structure of claim 11, wherein the liner is comprised of a material with a durometer of 5 A to 90 A.

13. The valve structure of claim 1, further comprising a cover connected to the outside mask side, wherein the cover introduces an additional change of direction to the expiratory airflow conduit that is greater than or equal to 75 degrees.

14. The valve structure of claim 13, wherein the cover comprises a sound absorbing liner.

15. The valve structure of claim 1, wherein the inspiratory valve comprises an inspiratory valve membrane made of a sound absorbing material.

16. The valve structure of claim 1, wherein the expiratory valve comprises an expiratory valve membrane made of a sound absorbing material.

* * * * *